United States Patent
Lebedev

(10) Patent No.: US 7,928,269 B2
(45) Date of Patent: Apr. 19, 2011

(54) PROCESS FOR SEPARATING TERTIARY ALCOHOLS FROM SECONDARY ALCOHOLS FROM PINE OIL

(75) Inventor: Mikhail Y. Lebedev, Jacksonville, FL (US)

(73) Assignee: LyondellBasell Flavors and Fragrances, LLC, Houston, TX (US)

( * ) Notice: Subject to any disclaimer, the term of this patent is extended or adjusted under 35 U.S.C. 154(b) by 232 days.

(21) Appl. No.: 12/317,874

(22) Filed: Dec. 30, 2008

(65) Prior Publication Data

US 2010/0168479 A1  Jul. 1, 2010

(51) Int. Cl.
 *C07C 35/00* (2006.01)
(52) U.S. Cl. .................. 568/875; 568/827; 568/868
(58) Field of Classification Search .................. None
See application file for complete search history.

(56) References Cited

U.S. PATENT DOCUMENTS

| | | |
|---|---|---|
| 1,743,403 A | 1/1930 | Smith |
| 1,772,546 A | 8/1930 | Humphrey |
| 1,800,862 A | 4/1931 | Humphrey |
| 1,915,388 A | 6/1933 | Smith |
| 1,928,020 A | 9/1933 | Humphrey |
| 1,932,183 A | 10/1933 | Humphrey |
| 1,945,501 A | 1/1934 | Humphrey |
| 1,961,398 A | 6/1934 | Smith |
| 1,980,030 A | 11/1934 | Blagden et al. |
| 2,011,707 A | 8/1935 | Borglin |
| 2,016,576 A | 10/1935 | Palmer |
| 2,050,671 A | 8/1936 | Sheffield |
| 2,052,743 A | 9/1936 | Bibb |
| 2,136,000 A | 11/1938 | Borglin |
| 2,151,769 A | 3/1939 | Humphrey |
| 2,178,349 A | 10/1939 | Sheffield |
| 2,423,545 A | 7/1947 | Aeschbach |
| 2,521,399 A | 9/1950 | Norton |
| 2,628,258 A | 2/1953 | Sapp et al. |
| 2,898,380 A | 8/1959 | Herrlinger et al. |
| 3,281,479 A | 10/1966 | Arakawa et al. |
| 3,661,978 A | 5/1972 | Gradeff et al. |
| 3,729,503 A | 4/1973 | Gribou et al. |
| 7,355,066 B1 | 4/2008 | Johnson et al. |

FOREIGN PATENT DOCUMENTS

| | | |
|---|---|---|
| DE | 4111900 | 10/1992 |
| JP | 9-278692 | 10/1997 |
| JP | 9-278693 | 10/1997 |

OTHER PUBLICATIONS

Palmer, R.C., Soovents form Pine, 1943, Industrial and Engineering Chemistry, vol. 35, No. 10, pp. 1023-1025.*
U.S. Appl. No. 12/317,903, filed Dec. 30, 2008, Lebedev.
Kirk-Othmer, "Terpenoids—α-Pinene Manufacture," *Kirk-Othmer Encyclopedia of Chemical Technology*, vol. 23, p. 838-839 (1997).
Kirk-Othmer, "Terpenoids—Monoterpene Alcohols," *Kirk-Othmer Encyclopedia of Chemical Technology*, vol. 23, p. 853-855 (1997).
S. Sabetay et al., Determination of Primary Alcohols and Certain Secondary Alcohols by means of Phthalisation and Identification of Esterifiable Alcohols in the Form of Acid Phthalates, *Ann. Chim. Anal.*, vol. 19, p. 285-289 (1937) from Abstracts of Chemical Papers.
R. Delaby et al., "Determination of Free Primary and Secondary Alcohols in the presence of Tertiary Alcohols in Essential Oils by Acetylation in Pyridine," *Bull. Soc. Chim.*, vol. 2, p. 1716-1724 (1935) from Abstracts of Chemical Papers.

* cited by examiner

*Primary Examiner* — Porfirio Nazario Gonzalez
*Assistant Examiner* — Yate K Cutliff
(74) *Attorney, Agent, or Firm* — Novak Druce + Quigg LLP; Michael P. Byrne

(57) ABSTRACT

A process for separating at least one tertiary alcohol from at least one secondary alcohol from pine oil, the process comprising:
 reacting the pine oil comprising the at least one secondary alcohol and the at least one tertiary alcohol with at least one $C_3$-$C_{30}$ carboxylic acid ester, and at least one base, wherein the secondary alcohol is esterified to produce at least one secondary ester, with the proviso that the base is not a hydroxide; and
 separating the tertiary alcohol from the secondary ester.

20 Claims, No Drawings

PROCESS FOR SEPARATING TERTIARY ALCOHOLS FROM SECONDARY ALCOHOLS FROM PINE OIL

FIELD OF INVENTION

The present inventive subject matter generally relates to a novel process for separating tertiary alcohols from secondary alcohols from pine oil.

BACKGROUND OF INVENTION

Pine oil, which can be derived as an essential oil from *Pinus sylvestris*, or alternatively, produced synthetically by acid-catalyzed reactions of terpenic hydrocarbons, alcohols, or diols in an aqueous media, comprises a variety of components, including a variety of terpenic alcohols. Of these terpenic alcohols, terpineol, which is a mixture of several tertiary alcohol isomers, including α-terpineol, β-terpineol, γ-terpineol, and 4-terpineol, has a pleasant floral odor similar to lilac and is widely used in high quality grades in consumer products in the fragrance and flavor industry. Along with terpineol, which has a boiling point of approximately 219° C. at normal pressure, several secondary terpenic alcohols, including fenchol and borneol which have boiling points of approximately 201° C. and 213° C. at normal pressure, respectively, are present in untreated pine oil, as well as other constituents, including various other terpenic alcohols, terpenic carbonyl compounds, terpene hydrocarbons, water, and other impurities. Separating terpineol from these and other constituents, as well as other low boiling impurities in pine oil, can be done relatively effectively and efficiently by employing traditional separation techniques given the differences in boiling points and solubilities.

However, although terpineol can be readily separated from water and other low boiling constituents in pine oil, terpineol cannot be readily separated from the secondary alcohols in pine oil, particularly fenchol and borneol. This is due to all three components having relatively similar boiling points, which does not allow the components to be separated easily by traditional separation techniques, particularly through distillation. Specifically, separating terpineol from borneol is an especially difficult task, since borneol co-distills with terpineol. Therefore, in order to sufficiently separate borneol from terpineol, multiple distillations or multiple other physical separations are usually required, which are not only time consuming, but are also energy inefficient, expensive to perform, can create a large amount of waste, and can denature the original terpineol in the pine oil, thus reducing the overall terpineol yield. Additionally, in order to produce high grade quality terpineol for acceptance by the consumer products industry, the terpineol has to satisfy strict requirements for purity, which is usually approximately 99% pure, as well as match industry odor standards. Accordingly, even relatively small amounts of impurities, including fenchol and borneol, can prevent a batch of terpineol from being considered high grade quality for use in consumer products.

Attempts have been made in the past to sufficiently separate the constituents of pine oil, including the processes outlined in U.S. Pat. Nos. 1,980,030, 2,050,671, and 1,800,862. In particular, the process outlined in U.S. Pat. No. 1,980,030 utilizes ortho-phosphoric acid to react with the terpenic or hydroaromatic alcohols in pine oil to produce the resultant phosphoric acid addition compounds. The resultant phosphoric acid addition compounds can then be separated from the pine oil through extraction, and then saponified back to the original alcohols. However, although the process of U.S. Pat. No. 1,980,030 generally separates the alcohols present in pine oil from the non-alcohols, the process does not allow one to separate the individual alcohols from one another, particularly tertiary alcohols from the other terpenic alcohols in pine oil.

With respect to U.S. Pat. No. 2,050,671, the process therein utilizes boric acid to separate both secondary and tertiary alcohols from pine oil. In particular, the process of U.S. Pat. No. 2,050,671 reacts boric acid with the terpenic alcohols in pine oil to produce the corresponding borates. The borates can then be separated from the pine oil by distillation, and then saponified back to the original alcohols. However, as with U.S. Pat. No. 1,980,030, although the process of U.S. Pat. No. 2,050,671 generally separates terpenic alcohols from non-alcohols present in pine oil, the process does not allow one to separate individual alcohols from one another, particularly tertiary alcohols from the other terpenic alcohols in pine oil.

As for U.S. Pat. No. 1,800,862, the process therein separates secondary alcohols from pine oil, including borneol and fenchol. In particular, the process of U.S. Pat. No. 1,800,862 begins with either preliminarily fractionating the pine oil to obtain fractions in which the secondary alcohols are concentrated, thereby removing most of the other constituents, including terpineol, or dehydrating the pine oil to remove the terpineol. After the secondary alcohols have been further concentrated, the secondary alcohols are then esterified with an organic acid and an acid catalyst, preferably hydrochloric acid, and recovered through distillation. However, although this process separates the secondary alcohols from pine oil, the terpineol is irrevocably destroyed by hydration.

Therefore, there remains a need in the art for a process to effectively and efficiently separate tertiary alcohols from the other constituents in pine oil. In particular, there remains a need in the art for a process to effectively and efficiently separate tertiary alcohols from secondary alcohols in pine oil.

SUMMARY OF INVENTION

The present inventive subject matter generally relates to a novel process for separating secondary alcohols and tertiary alcohols from pine oil. In this regard, an embodiment of the present inventive subject matter relates to a process for separating at least one tertiary alcohol from at least one secondary alcohol from pine oil, the process comprising:

reacting the pine oil comprising the at least one secondary alcohol and the at least one tertiary alcohol with at least one $C_3$-$C_{30}$ carboxylic acid ester, and at least one base, wherein the secondary alcohol is esterified to produce at least one secondary ester, with the proviso that the base is not a hydroxide; and separating the tertiary alcohol from the secondary ester.

Another embodiment of the present inventive subject matter relates to a process for separating terpineol from borneol and fenchol in pine oil, the process comprising:

treating the pine oil comprising the borneol, the fenchol, and the terpineol to substantially remove water present in the pine oil to produce a substantially anhydrous pine oil mixture;

substantially removing the fenchol from the substantially anhydrous pine oil mixture to produce a borneol and terpineol mixture;

reacting the borneol and terpineol mixture with at least one $C_3$-$C_{30}$ carboxylic acid ester and at least one base, wherein the borneol is esterified to produce a borneol ester, with the proviso that the base is not a hydroxide; and separating the terpineol from the borneol ester.

Additionally, in yet another embodiment, the present inventive subject matter relates to a process for producing fragrance-quality terpineol, the process comprising:

distilling pine oil comprising water, terpenes, fenchol, borneol, and terpineol to substantially remove the water, the terpenes, and the fenchol to produce a mixture comprising a majority of borneol and terpineol;

reacting the mixture comprising the majority of the borneol and the terpineol with at least one $C_3$-$C_{30}$ carboxylic acid ester comprising at least one $C_7$-$C_{20}$ carboxylic acid moiety and at least one strong organic base, wherein the majority of the borneol is esterified to produce a borneol ester; and distilling the terpineol from the borneol ester, wherein the distilled terpineol comprises at least 95% by weight of the terpineol.

DETAILED DESCRIPTION OF INVENTION

Definitions:

As used herein, the phrase "substantially remove", and like phrases, mean the component being removed is present at less than about 5% by weight, preferably less than about 1% by weight, and most preferably less than about 0.5% by weight after being removed.

As used herein, the phrase "substantially anhydrous", and like phrases, mean the water content is less than about 1% by weight, preferably less than about 0.5% by weight, and most preferably less than about 0.1% by weight after being removed.

Process:

The novel process of the present inventive subject matter allows for the separation of at least one tertiary alcohol from at least one secondary alcohol from pine oil. In a particular embodiment, the novel process of the present inventive subject matter relates to a process for separating at least one tertiary alcohol from at least one secondary alcohol from pine oil, the process comprising:

reacting the pine oil comprising the at least one secondary alcohol and the at least one tertiary alcohol with at least one $C_3$-$C_{30}$ carboxylic acid ester, and at least one base, wherein the secondary alcohol is esterified to produce at least one secondary ester, with the proviso that the base is not a hydroxide; and separating the tertiary alcohol from the secondary ester.

As discussed above, pine oil is composed of a variety of constituents, including secondary alcohols such as fenchol and borneol, as well as tertiary alcohols, such as terpineol, which can have high boiling points within approximately ±18° C. of each other. Therefore, separating the tertiary alcohols from the secondary alcohols can often be difficult, time consuming, expensive, and inefficient by conventional methods, including conventional chemical extraction and distillation methods. Accordingly, one of the benefits the present process can provide is a novel process in which tertiary alcohols, including terpineol, can be separated from pine oil, including separating the terpineol from the secondary alcohols in pine oil, which include fenchol, borneol, and mixtures thereof. In a preferred embodiment of the present process, the terpineol separated from the pine oil can include α-terpineol, γ-terpineol, and mixtures thereof.

In a particular embodiment, the process of the present subject matter separates at least one tertiary alcohol, including terpineol, from at least one secondary alcohol from pine oil, by reacting the secondary alcohol in the pine oil with at least one $C_3$-$C_{30}$ carboxylic acid ester and at least one base to convert the secondary alcohol into a corresponding secondary ester, with the proviso that the base is not a hydroxide, including hydroxides selected from alkali metal hydroxides and alkali earth metal hydroxides. The tertiary alcohol can then be separated from the secondary ester in the pine oil by traditional separation methods, including, but not limited to, distillation with or without vacuum, and crystallization methods. In a particularly preferred embodiment, the secondary alcohol in the pine oil can be borneol, fenchol, and mixtures thereof, and the secondary ester can be borneol ester, fenchol ester, and mixtures thereof.

Furthermore, with previous techniques, in order to obtain tertiary alcohols with sufficient purity from pine oil, multiple traditional separation methods needed to be performed in order to separate the tertiary alcohols in pine oil, including terpineol, from the secondary alcohols in pine oil, including borneol, fenchol, and mixtures thereof. However, even after performing multiple traditional separations, many times the resultant tertiary alcohols produced are not of sufficient purity. Alternatively, preferred embodiments of the present process can produce at least 95% by weight, and preferably at least 99% by weight of at least one tertiary alcohol. Additionally, in other preferred embodiments, the process of the present subject matter can produce a tertiary alcohol comprising terpineol, wherein the terpineol comprises 25% by weight, and preferably 35% by weight of α-terpineol. In yet other embodiments of the present process, after the secondary alcohols are esterified into the corresponding secondary esters, the tertiary alcohol, including terpineol, can be separated from the secondary ester by traditional separation methods. In particular embodiments of the present process, after the secondary alcohols are esterified into the corresponding secondary esters, the tertiary alcohol, including terpineol, can be separated from the secondary ester in a single separation step or multiple separate steps, including but not limited to, a single distillation or multiple distillations.

Pine Oil:

In addition to the benefits discussed above, another benefit the present process can have is that any type of pine oil can be used, including "crude" (i.e., untreated) pine oil, or pre-treated pine oil, and the pine oil can be derived from natural sources such as *Pinus sylvestris*, or derived synthetically. Crude pine oil can generally have a starting tertiary alcohol content, including terpineol, ranging from about 20% to about 80% by weight, with the remaining content being composed of various impurities, including, but not limited to, water, other terpenic alcohols, including secondary terpenic alcohols such as fenchol and borneol, terpenic carbonyl compounds, pinenes, pinanols, and terpene hydrocarbons. In particular embodiments of the present process, crude pine oil which has not undergone any pretreatment can be used.

Alternatively, in other embodiments of the present process, pre-treated pine oil can be used, wherein the pre-treated pine oil can generally have a higher or lower tertiary alcohol content, including generally a higher or lower terpineol content than that of crude pine oil. In particular, the pine oil used in the present process can be treated in a variety of ways before use, including but not limited to, treating the pine oil before use by separating various components from the pine oil, including lower boiling impurities. Generally, components having a boiling point lower than approximately 200° C. at normal pressure, including water and low boiling impurities, can be separated before using the pine oil in the present process in a variety of ways, including separation processes utilizing differences in boiling points, including but not limited to distillation with or without a vacuum, differences in crystallization, differences in solubilites, and differences in polarity, which are well-known in the art. Examples of separation processes can be found in the *Kirk-Othmer Encyclopedia of Chemical Technology*, 5th edition, published by John Wiley & Sons.

Additionally, in particularly preferred embodiments of the present process, the pine oil can be pre-treated to substantially remove any number of various impurities, including, but not limited to, water, terpenic carbonyl compounds, pinenes, pinanols, and terpene hydrocarbons. Furthermore, in particular preferred embodiments of the present process, the pine oil can be treated to substantially remove at least the water present in the pine oil before being used. Additionally, in other particular preferred embodiments of the present process, the pine oil can be pre-treated to substantially remove the impurities previously mentioned, as well as various terpenic alcohols, including, but not limited to fenchol.

In embodiments in which the pine oil is treated to substantially remove the water present in the pine oil before the process is carried out, the amount of water substantially removed can be, but is not required to be, such that the resultant treated pine oil is substantially anhydrous. In yet another embodiment of the present process, the pine oil is treated to substantially remove at least the water and the fenchol present before the pine oil is used. Furthermore, in yet another embodiment of the present process, the pine oil is treated to substantially remove at least the water, the terpenes, and the fenchol present before the pine oil is used. Moreover, in particular preferred embodiments of the present process, crude pine oil can be pre-treated to remove a front cut of the pine oil with boiling temperatures up to about 201° C. at normal pressure, wherein the front cut is composed of various lower boiling impurities, including, but not limited to water, terpenic carbonyl compounds, pinenes, pinanols, terpene hydrocarbons, and fenchol. Accordingly, when a front cut with boiling temperatures up to about 201° C. at normal pressure is removed from the pine oil, the resultant mixture comprises a majority of terpineol and borneol. The resultant mixture comprising a majority of terpineol and borneol can then be reacted with at least one $C_3$-$C_{30}$ carboxylic acid ester and at least one base to produce a mixture comprising terpineol and at least one borneol ester, with the proviso that the base is not a hydroxide, including hydroxides selected from alkali metal hydroxides and alkali earth metal hydroxides, with the terpineol then being separated from the borneol ester.

However, regardless of whether the pine oil used in the present process is crude pine oil or pre-treated pine oil, whether the pine oil is derived from natural sources or produced synthetically, as well as regardless to the amount of tertiary alcohol and terpineol content in the pine oil used, one of the benefits of the present process is that the process can separate the tertiary alcohols, including terpineol, from the secondary alcohols present in the pine oil.

Carboxylic Acid Ester:

The carboxylic acid esters useful for the present process are those that can react with a secondary alcohol in the presence of a base to produce a corresponding secondary ester. Accordingly, various carboxylic acid esters can be used with the present process, including using a single carboxylic acid ester, or a mixture of various carboxylic acid esters, with the carboxylic acid esters including monobasic, dibasic, polybasic carboxylic acid esters, or mixtures thereof.

Generally, the carboxylic acid esters useful for the present process can be at least one $C_3$-$C_{30}$ carboxylic acid ester comprising a $C_2$-$C_{20}$ carboxylic acid derived moiety, and a $C_1$-$C_{10}$ alcohol derived moiety. In preferred embodiments of the present process, the carboxylic acid ester used can be at least one $C_8$-$C_{25}$ carboxylic acid ester comprising a $C_7$-$C_{20}$ carboxylic acid derived moiety, and a $C_1$-$C_5$ alcohol derived moiety, and in particularly preferred embodiments of the present process, the carboxylic acid ester can be at least one $C_8$-$C_{23}$ carboxylic acid ester comprising a $C_7$-$C_{20}$ carboxylic acid derived moiety, and a $C_1$-$C_3$ alcohol derived moiety.

Alternatively, carboxylic acid esters of the tertiary alcohols being separated can be used in the present process. In this regard, preferred carboxylic acid esters can include terpineol carboxylic acid esters.

Non-limiting examples of preferred carboxylic acid esters include isopropyl myristate; biodiesel; soy solvent; ME-810 available from Peter Cremer NA, LP; ME-1095 available from Peter Cremer NA, LP; ME-1618 available from Peter Cremer NA, LP; ME-1695 available from Peter Cremer NA, LP, ME-1897 available from Peter Cremer NA, LP; ME-1897V available from Peter Cremer NA, LP; ME-1820 available from Peter Cremer NA, LP; ME-S1885 available from Peter Cremer NA, LP; ME-S1892 available from Peter Cremer NA, LP; SG 1100 available from Ag Environmental Products L.L.C.; SG 2500 available from Ag Environmental Products L.L.C.; esters of aromatic acids, including benzoic acid and naphthalic acid; esters of polybasic acids, including tartaric acid and citric acid; and mixtures thereof.

The amount of carboxylic acid ester or esters used in the present process can be dependent upon the type of pine oil used. In particular, if crude pine oil is used, then generally a larger amount of at least one carboxylic acid ester can be used. Alternatively, if pre-treated pine oil is used, especially pine oil which has been pre-treated to separate a front cut with boiling temperatures up to about 201° C. at normal pressure, then generally a lesser amount of at least one carboxylic acid ester can be used. In general, the amount of the carboxylic acid ester or esters used is dependent upon the concentration of secondary alcohols present in the pine oil to be subjected to the present process. Therefore, the higher the concentration of secondary alcohols in the pine oil to be treated, the greater the amount of at least one carboxylic acid ester should be used. Contrastingly, the lower the concentration of the secondary alcohols in the pine oil to be treated, the lesser the amount of at least one carboxylic acid ester should be used. Preferably, the molar concentration of carboxylic acid ester or esters used to the molar concentration of secondary alcohols in the pine oil can be approximately 1:1.5 to 10:1. However, regardless of the concentration of secondary alcohols present in the pine oil used in the present process, at least one carboxylic acid ester can be added in any amount, including but not limited to, an amount in excess.

In this regard, in preferred embodiments of the present process, at least one $C_3$-$C_{30}$ carboxylic acid ester is added to pine oil with a base, wherein the $C_3$-$C_{30}$ carboxylic acid esterifies at least one secondary alcohol in the pine oil to produce a secondary ester. In particularly preferred embodiments of the present process, at least one $C_3$-$C_{30}$ carboxylic acid ester is added to pine oil, the pine oil comprising at least a mixture of terpineol and borneol, wherein the $C_3$-$C_{30}$ carboxylic acid ester esterifies a majority of the borneol into a corresponding borneol ester. Additionally, in yet further particularly preferred embodiments of the present process, at least one $C_3$-$C_{30}$ carboxylic acid ester is added to pine oil, the pine oil comprising at least a mixture of terpineol, borneol, and fenchol, wherein the $C_3$-$C_{30}$ carboxylic acid ester esterifies a majority of the borneol and fenchol into at least one corresponding borneol ester and at least one fenchol ester.

Base:

The bases useful for the present process are those that can facilitate a reaction between a secondary alcohol and a carboxylic acid ester, with the proviso that the base is not a hydroxide, including hydroxides selected from alkali metal hydroxides and alkali earth metal hydroxides. Therefore, various bases can be used with the present process, including the use of a single base, as well as a mixture of bases. Generally, the bases useful for the present process can be at least one strong base capable of establishing an equilibrium between reactants, with the base or bases comprising a pKa of the corresponding conjugate acid greater than about 9, more preferably greater than about 15. In preferred embodiments of the present process, the base or mixture of bases can comprise a pKa ranging from about 9 to about 40, and preferably from about 15 to about 25.

In particular embodiments of the present process, the base can be at least one organic base, preferably at least one strong organic base, including at least one alkoxide, and salts thereof. Preferred alkoxides, and salts thereof, include at least one alkali metal alkoxide, alkali earth metal alkoxide, and mixtures thereof. Particularly preferred alkoxides include, but are not limited to, sodium methoxide, sodium ethoxide, sodium isopropoxide, potassium methoxide, potassium ethoxide, potassium isopropoxide, and mixtures thereof.

Additionally, other organic bases can be used for the present process. Non-limiting examples of additionally preferred organic bases include 1,8-diazabicyclo[5.4.0]undec-7-ene (DBU), 1,4-diazabicyclo[2.2.2]octane (DABCO), 4-(dimethylamino)pyridine (DMAP), and phosphazene bases, including, but not limited to, 2-tert-Butylimino-2-diethylamino-1,3-dimethylperhydro-1,3,2-diazaphosphorine, 2-tert-Butylimino-2-diethylamino-1,3-dimethylperhydro-1,3,2-diazaphosphorine, 2-tert-Butylimino-2-diethylamino-1,3-dimethylperhydro-1,3,2-diazaphosphorine, tert-Butyl-imino-tris(dimethylamino)phosphorane, Imino-tris(dimethylamino)phosphorane, 1,1,3,3,3-Pentakis(dimethylamino)-1$\lambda^5$,3$\lambda^5$-diphosphazene 1-oxide, phosphazene base $P_1$-t-Bu, phosphazene base $P_2$-t-Bu solution, phosphazene base $P_4$-t-Bu solution, phosphazene base $P_1$-t-Bu-tris(tetramethylene), phosphazene base $P_2$-Et, phosphazene base $P_1$-t-Oct, phosphazene base $P_4$-t-Oct solution, 1,8-bis(dimethylamino)naphthalene, and mixtures thereof.

Alternatively, in other particular embodiments of the present process, the base can be at least one inorganic base, preferably a strong inorganic base, with the proviso that the base is not a hydroxide, including hydroxides selected from alkali metal hydroxides and alkali earth metal hydroxides. Preferred inorganic bases include sodium oxide, potassium oxide, calcium oxide, magnesium oxide, sodium hydride, sodium amide, sodium carbonate, potassium carbonate, cesium carbonate, metallic sodium, and mixtures thereof. Furthermore, ion-exchange resins such as Amberlite™ ion-exchange resins, including but not limited to Amberlite™ IRA-67, can also be used alone or in conjugation with other bases.

The amount of base or bases used in the present process can be dependent upon the type of pine oil used. In particular, as with the amount of carboxylic acid ester or esters used, if crude pine oil is used, then generally a larger amount of at least one base can be used. Additionally, since water may denature the base, the higher the water concentration is in the pine oil, the more base may be needed. Alternatively, if pre-treated pine oil is used, especially pine oil which has been pre-treated to separate a front cut with boiling temperatures up to about 201° C. at normal pressure, then generally a lesser amount of at least one base can be used. In general, the amount of base used can be dependent upon the concentration of water present in the pine oil, the relative strength and concentration of the base or bases used, and the concentration of secondary alcohols in the pine oil. Therefore, preferably, the molar concentration of the base or bases used to the molar concentration of secondary alcohols in the pine oil can be approximately about 1:1 to about 1:20, more preferably about 1:3 to about 1:10.

Alternatively, in additional embodiments of the present process, at least one base can be used in excess. However, if at least one base is used in excess, in preferred embodiments of the present process, the excess base is substantially neutralized before the tertiary alcohol is separated from the pine oil. Accordingly, if at least one base is used in excess, in a preferred embodiment of the present process, the excess base is neutralized such that the pine oil comprises a pH less than about 9, preferably less than about 8, and most preferably the pine oil comprises a pH ranging from about 4 to about 8.

EXAMPLES

The following examples are illustrative of preferred compositions, and are not intended to be limitations thereon. All product composition percentages are based on totals equal to 100% by gas chromatography analysis, and yield percentages are based on totals equal to 100% by weight, unless otherwise specified.

Test Methods:

Purity and composition percentages were determined using gas chromatography without a solvent on a 30-meter capillary column with a SPB-1 stationary phase on an Agilent Technologies 6890N GC.

Odor evaluations were performed by a panel of trained professionals comparing the odor profile and quality of compositions obtained against the odor and quality industry standard for terpineol.

Example 1

Crude pine oil (1709.4 g; terpineol: 59.8%; fenchol: 7.0%; borneol: 3.4%) is vacuum stripped to remove water, light hydrocarbons, and fenchol. The remaining pot content (1000 g; by GC: terpineol: 96.3%; fenchol: 0.1%; borneol: 2.6%) is mixed with ME-810 (78.0 g; mixture of fatty acid methyl esters, available from Peter Cremer NA, LP) and sodium methoxide (7.8 g of 30% solution in methanol). The resulting mixture is stirred for 3 h at 105° C., 30 mm Hg to remove methanol. GC of the reaction mixture shows that most of borneol has reacted (terpineol: 88.1%; fenchol: 0%; borneol: 0.58%). The reaction mixture is distilled using a 4' column at 12-20 mm Hg to give fourteen cuts and 180 g of residue. A blend of cuts 4-14 (703 g) contains terpineol: 99.4%; fenchol: 0%; borneol: 0.51%. The blend passes an odor test when compared with an industry standard. Yield of in-spec α-terpineol: 41%.

Example 2

Crude pine oil (1695 g; terpineol: 62.2%; fenchol: 7.85%; borneol: 2.4%) is vacuum stripped to remove water, light hydrocarbons, and fenchol. The remaining pot content (1017 g; by GC: terpineol: 93.11%; fenchol: 0.2%; borneol: 2.5%) is mixed with biodiesel ME-1885 (129.0 g; mixture of fatty acid methyl esters, available from Peter Cremer NA, LP) and sodium methoxide (8.0 g of 30% solution in methanol). The resulting mixture is stirred for 3 h at 105° C., 20 mm Hg to methanol. The reaction mixture is distilled at 15-20 mm Hg to give eight cuts and 292 g of residue. A blend of cuts 2-8 (737.6 g) contains terpineol: 99.01%; fenchol: 0.01%; borneol: 0.64%. The blend passes an odor test when compared with an industry standard. Yield of in-spec α-terpineol: 43.5%.

Example 3

Crude pine oil (1665.2 g; terpineol: 62.6%; fenchol: 7.0%; borneol: 2.3%) is vacuum stripped to remove water, light hydrocarbons, and fenchol. The remaining pot content (1000 g; by GC: terpineol: 95.1%; fenchol: 0.06%; borneol: 1.81%) is mixed with ME-1885 (97.0 g; mixture of fatty acid methyl esters, available from Peter Cremer NA, LP) and sodium methoxide (6.0 g of 30% solution in methanol). The resulting mixture is stirred for 1.5 h at 100° C., 20 mm Hg to remove methanol. The reaction mixture is distilled using a 4' column at 20 mm Hg to give ten cuts and 209 g of residue. A blend of cuts 4-10 (589.9 g) contains terpineol: 99.13%; fenchol: 0%; borneol: 0.24%. Yield of in-spec $\alpha$-terpineol: 35.4%.

Example 4

Crude pine oil (3385 g; terpineol: 51.3%; fenchol: 7.4%; borneol: 2.1%) is stripped using a 4' column to provide fourteen cuts. Cuts 9-14, which contain no light hydrocarbons, water, or residue, are combined. The resulting blend (pH 5.14; 0.018% water) is used in the next step.

The purified terpineol (1073 g; terpineol: 94.7%; fenchol: 0.54%; borneol: 2.69%) is mixed with ME-1885 (171 g; mixture of methyl fatty esters, available from Peter Cremer NA, LP) and sodium methoxide (2.1 g of 30% solution in methanol). After heating for 2 h at 105° C., 20-80 mm Hg, GC analysis of the reaction mixture shows about 1.3% borneol. Additional sodium methoxide (2 g) is added and heating at 105° C. continues for 1.5 h. The reaction mixture is then distilled (21 mm Hg) to give eleven cuts and 386 g of residue. A blend of cuts 6-9 (382.8 g, 35.7% yield contains: terpineol: 99.6%; fenchol: 0%; borneol: 0.06%) is odor-approved. Another blend of cuts 3-11 (715.8 g; 66.7% yield) has an acceptable GC composition (terpineol: 99.3%; fenchol: 0%; borneol: 0.28%) but does not pass the odor test. The odor of this blend can be upgraded to passing using a fast re-distillation.

Example 5

A mixture of crude terpineol (4114 g; GC: $\alpha$- and $\gamma$-terpineol: 63.8%; fenchol: 8.1%; borneol: 2.5%; moisture: 0.42%; pH: 6.84) and aqueous sodium hydroxide (7.6 g of 50% NaOH solution) is vacuum stripped to remove water, light hydrocarbons, and fenchol, with pressure gradually decreased from 100 to 20 mm Hg. Light hydrocarbons (1367 g) are distilled away, and the remaining pot contents (2649 g; moisture: 0.028%; pH 11.5; GC: $\alpha$- and $\gamma$-terpineol: 92.0%; fenchol: 0.55%; borneol: 2.54%) are cooled to 50° C. The pot content is reduced to 1696 g by removing a portion of the product. Isopropyl myristate (235.6 g) and sodium ethoxide solution (21% NaOEt in ethanol; 28.8 g) are then added. The resulting mixture is heated for 3 h at 105° C., 20 mm Hg to remove ethanol. Distillation at 15-20 mm Hg provides 15 cuts and 412 g of residue. A blend of cuts 3-15 (1198 g) contains $\alpha$- and $\gamma$-terpineol (99.2%); fenchol: (0%); and borneol (0.42%). The odor of this blend can be upgraded to passing using a fast re-distillation.

Example 6

Fast Re-distillation for Odor Upgrade

Re-distillation of the blend of cuts 2-10 from Example 5 (1233 g; GC: $\alpha$- and $\gamma$-terpineol: 98.9%; fenchol: 0%; borneol: 0.47%) under vacuum (20 to 15 mm Hg) provides 14 cuts and 31.5 g of residue. A blend of cuts 5-14 (920 g) is odor-approved and has the following composition by GC: $\alpha$- and $\gamma$-terpineol: 99.7%; fenchol: 0%; borneol: 0.29%.

Example 7

Purified terpineol (127.2 g; terpineol: 97.6%; fenchol: 0.02%; borneol: 1.07%), which contains no light hydrocarbons, water, or residue, is mixed with isopropyl myristate (11.95 g) and cesium carbonate (10.0 g). After heating for 7 h at 130° C., 30 mm Hg, GC analysis of the reaction mixture shows about 0.85% borneol. Additional heating at 130° C. continues for 32 h and GC analysis of the reaction mixture shows about 0.06% borneol. The reaction mixture is then distilled (10 mm Hg) to give 114.0 g of distillate and 30.8 g of residue. Distillate (114.0 g, 89.6% yield) contains: terpineol: 99.0%; fenchol: 0%; borneol: 0.06% but does not pass the odor test. The odor of this blend can be upgraded to passing using a fast distillation.

Comparative Example 1

Crude Pine Oil Distillation without Carboxylic Acid Ester and Base

Crude pine oil (3865 g; GC: terpineol: 63.9%; fenchol: 8.06%; borneol: 2.34%) is distilled on 4' column at 10-20 mm Hg with a split ratio (R:R) of 40:8, corresponding to a take-off rate of 80.5 g/hr, to give 17 cuts. A blend of cuts 14-17 cuts (850 g) has a satisfactory GC analysis (terpineol: 99.1%; fenchol: 0%; borneol: 0.73%), but the yield is too low (22 wt. %). Moreover, its odor does not match that of the industry standard. This example shows that a single distillation of crude pine oil is inefficient for producing high-quality terpineol.

Comparative Example 2

Crude Pine Oil Distillation without Carboxylic Acid Ester and Base

Crude pine oil (1697.2 g; GC: terpineol: 62.1%; fenchol: 7.85%; borneol: 2.4%) is distilled on 4' column at 10-20 mm Hg with a split ratio (R:R) of 40:6, corresponding to a take-off rate of 57.2 g/hr, to give 17 cuts. A blend of cuts 12-17 cuts (550.2 g) has a satisfactory GC analysis (terpineol: 99.14%; fenchol: 0%; borneol: 0.68%), but even with the slower take-off rate, the yield is too low (32.4 wt. %). Moreover, its odor does not match that of the industry standard. This example shows that even a slower and longer single distillation of crude pine oil is inefficient for producing high-quality terpineol.

Comparative Example 3

Crude Pine Oil Distillation with Sodium Hydroxide

A mixture of crude pine oil (100 g, dehydrated by distillation), ME-1095 fatty acid methyl ester mixture (6.0 g, product of Peter Cramer NA, LP), and a solution of sodium hydroxide (1.1 g) in methanol (10 g) is kept at 110° C., 30 mm Hg with stirring for 140 min. About two-thirds of the ME-1095 reacts with NaOH to produce sodium salts of fatty acids, and only 0.06% of the corresponding esters form. This example shows that sodium hydroxide is an inefficient catalyst for the disclosed esterification reaction.

Comparative Example 4

Crude Pine Oil Distillation with Acid

Crude pine oil (138.8 g; dehydrated by vacuum stripping and containing terpineol: 94.0%; fenchol: 0.29%; borneol: 3.66%) is heated with ME-810 (12.4 g; mixture of methyl fatty acid esters, available from Peter Cremer NA, LP) and methanesulfonic acid (1.0 g) at 100° C., 30-60 mm Hg for 10 h. GC of the reaction mixture shows: terpineol: 19.9%; borneol: 1.85%; terpene alcohol fatty esters: 2%. Limonene and terpinolene, formed by acid-catalyzed dehydration of terpineol, account for 65% of the reaction mixture. Distillation of the reaction mixture gives 108 g of material containing 1.85% of borneol and 18.5% of terpineol. This example shows that methanesulfonic acid is an unacceptable catalyst for the transesterification.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

I claim:

1. A process for separating at least one tertiary alcohol from at least one secondary alcohol from pine oil, the process comprising:
   reacting the pine oil comprising the at least one secondary alcohol and the at least one tertiary alcohol with at least one $C_3$-$C_{30}$ carboxylic acid ester, and at least one base, wherein the secondary alcohol is esterified to produce at least one secondary ester, with the proviso that the base is not a hydroxide; and
   separating the tertiary alcohol from the secondary ester.

2. The process of claim 1, wherein the pine oil further comprises water, and before the pine oil is reacted with the $C_3$-$C_{30}$ carboxylic acid ester and the base, the pine oil is treated to substantially remove the water.

3. The process of claim 1, wherein the secondary alcohol is borneol, fenchol, or mixtures thereof.

4. The process of claim 1, wherein the secondary ester is borneol ester, fenchol ester, or mixtures thereof.

5. The process of claim 1, wherein the tertiary alcohol is terpineol.

6. The process of claim 1, wherein the tertiary alcohol is α-terpineol, γ-terpineol, or mixtures thereof.

7. The process of claim 1, wherein the $C_3$-$C_{30}$ carboxylic acid ester comprises a $C_7$-$C_{20}$ carboxylic acid moiety.

8. The process of claim 1, wherein the $C_3$-$C_{30}$ carboxylic acid ester is isopropyl myristate.

9. The process of claim 1, wherein the base is a strong organic base.

10. The process of claim 1, wherein the base is a strong inorganic base, with the proviso that the base is not a hydroxide.

11. The process of claim 1, wherein the base is an alkoxide, an alkoxide salt, or mixtures thereof.

12. The process of claim 1, wherein the base is selected from sodium methoxide, sodium ethoxide, sodium isopropoxide, potassium methoxide, potassium ethoxide, potassium isopropoxide, sodium oxide, sodium hydride, sodium amide, calcium oxide, magnesium oxide, sodium carbonate, potassium carbonate, cesium carbonate, DBU (1,8-diazabicyclo[5.4.0]undec-7-ene), DABCO (1,4-diazabicyclo[2.2.2]octane), DMAP (4-(dimethylamino)pyridine), 1,8-bis(dimethylamino)naphthalene, phosphazene bases, and mixtures thereof.

13. The process of claim 1, wherein the tertiary alcohol is separated from the secondary ester by distillation.

14. The process of claim 1, wherein the process produces at least 95% by weight of at least one tertiary alcohol.

15. The process of claim 1, wherein the process produces at least 99% by weight of at least one tertiary alcohol.

16. A process for separating terpineol from borneol and fenchol in pine oil, the process comprising:
   treating the pine oil comprising the borneol, the fenchol, and the terpineol to substantially remove water present in the pine oil to produce a substantially anhydrous pine oil mixture;
   substantially removing the fenchol from the substantially anhydrous pine oil mixture to produce a borneol and terpineol mixture;
   reacting the borneol and terpineol mixture with at least one $C_3$-$C_{30}$ carboxylic acid ester and at least one base, wherein the borneol is esterified to produce a borneol ester, with the proviso that the base is not a hydroxide; and
   separating the terpineol from the borneol ester.

17. A process for producing fragrance-quality terpineol, the process comprising:
   distilling pine oil comprising water, terpenes, fenchol, borneol, and terpineol to substantially remove the water, the terpenes, and the fenchol to produce a mixture comprising a majority of borneol and terpineol;
   reacting the mixture comprising the majority of the borneol and the terpineol with at least one $C_3$-$C_{30}$ carboxylic acid ester comprising at least one $C_7$-$C_{20}$ carboxylic acid moiety and at least one strong organic base, wherein the majority of the borneol is esterified to produce a borneol ester; and
   distilling the terpineol from the borneol ester, wherein the distilled terpineol comprises at least 95% by weight of the terpineol.

18. The process of claim 17, wherein the distilled terpineol comprises at least 99% by weight of the terpineol.

19. The process of claim 17, wherein the distilled terpineol comprises at least 25% by weight of α-terpineol.

20. The process of claim 17, wherein the distilled terpineol comprises at least 35% by weight of α-terpineol.

* * * * *